United States Patent [19]
Chou et al.

[11] Patent Number: 6,039,565
[45] Date of Patent: Mar. 21, 2000

[54] COMBINED ULTRASONIC AND LASER DEVICE AND METHOD OF USE

[76] Inventors: Marilyn M. Chou; Herrick Tam; King J. J. Yu; Ken T. Yu, all of 900 Alice St., Oakland, Calif. 94607

[21] Appl. No.: 09/006,922

[22] Filed: Jan. 14, 1998

Related U.S. Application Data

[60] Provisional application No. 60/035,093, Jan. 14, 1997.
[51] Int. Cl.$^7$ ...................................................... A61C 1/07
[52] U.S. Cl. ............................... 433/29; 433/119; 433/215
[58] Field of Search .............................. 433/29 OR, 118, 433/119, 215

[56] References Cited

U.S. PATENT DOCUMENTS

| | | | |
|---|---|---|---|
| 4,169,984 | 10/1979 | Parisi | 433/119 |
| 4,725,232 | 2/1988 | Hatakeyama | 433/98 |
| 4,804,364 | 2/1989 | Dieras et al. | 433/86 |
| 4,940,411 | 7/1990 | Vassiliadis et al. | 433/29 |
| 5,328,365 | 7/1994 | Jacoby | 433/29 |

*Primary Examiner*—John J. Wilson
*Attorney, Agent, or Firm*—James J. Leary; Carol D. Titus

[57] ABSTRACT

A combined laser and ultrasonic device includes a combination laser and ultrasonic source, a control console and a combined laser and ultrasonic delivery handpiece. The system has three modes of operation: 1) laser energy only, 2) ultrasonic energy only and 3) combined laser and ultrasonic energy. All three modes of operation are controlled by a single foot-operated activation switch, which will operate the laser source, the ultrasonic source or both, depending on which mode the device is operating in according to a mode switch on the control console. The combined laser and ultrasonic delivery handpiece includes an ultrasonic transducer coupled to an ultrasonic vibrating tip, which is mounted in close proximity to a laser delivery wave guide, such as a flexible optical fiber. The combined laser and ultrasonic device can be used to perform a variety of surgical procedures, including an improved method of a laser excisional new attachment procedure (Laser E.N.A.P.), which is described for treatment of periodontal diseases.

22 Claims, 5 Drawing Sheets

COMBINED ULTRASONIC AND LASER DEVICE AND METHOD OF USE

RELATIONSHIP TO OTHER APPLICATIONS

This application claims the benefit of Provisional Patent Application 60/035,093, filed on Jan. 14, 1997.

FIELD OF THE INVENTION

This invention relates to a combined ultrasonic and laser device for surgical applications and to methods of treatment using this device. A specific example of an improved method of performing a laser excisional new attachment procedure for treatment of periodontal diseases using the device is described.

BACKGROUND OF THE INVENTION

A method of performing a laser excisional new attachment procedure (Laser E.N.A.P.) for treatment of periodontal diseases is described by Robert H. Gregg, D.D.S. and Delwin K. McCarthy, D.D.S in U.S. Pat. No. 5,642,997, issued Jul 1, 1997, entitled Laser Excisional New Attachment Procedure, which is incorporated herein by reference in its entirety. The procedure described uses separate laser and ultrasonic devices sequentially for laser excision of gingival tissue within a gingival pocket around a tooth, followed by ultrasonically descaling the root of the tooth, then by laser cauterization of the gingival pocket. The laser energy and ultrasonic energy are always separately applied in the procedure as described. The gingival tissue is then approximated to the root of the tooth for healing by secondary intention. This procedure is highly effective for reattachment of the gums or gingiva and for regeneration of the osteal attachment for a tooth which is threatened by periodontal disease.

SUMMARY OF THE INVENTION

In order to facilitate and to improve upon the Laser E.N.A.P. method described by Gregg and McCarthy the present invention provides a combined laser and ultrasonic device. The combined laser and ultrasonic device is a system which includes a combination laser and ultrasonic source and control console and a combined laser and ultrasonic delivery handpiece. The control console provides for three modes of operation: 1) laser energy only, 2) ultrasonic energy only and 3) combined laser and ultrasonic energy. The combined laser and ultrasonic delivery handpiece includes an ultrasonic transducer coupled to an ultrasonic vibrating tip, which is mounted in close proximity to a laser delivery wave guide, such as a flexible optical fiber, for directing the laser radiation and the ultrasonic vibration onto a common target area. The combined laser and ultrasonic device can be used to perform the standard Laser E.N.A.P. method as described by Gregg and McCarthy by alternating between the laser mode and the ultrasonic mode as required. Used in this manner, the combined laser and ultrasonic device facilitates the ability perform Laser E.N.A.P. by making the laser function and the ultrasonic function available in a single tool. The device also speeds up the procedure and makes it much more efficient because fewer instrument exchanges are needed. Eliminating the necessity of instrument exchanges also eliminates a great deal of complexity and confusion from the procedure which would have the desirable side effect of reducing the stress on the surgeon and his or her support staff.

Furthermore, the combined laser and ultrasonic mode of the device allows an improved method of performing Laser E.N.A.P. in which the laser energy and the ultrasonic energy are applied simultaneously to the gingival pocket. The results of this combination are synergistic, speeding up the action of the laser functions, as well as the ultrasonic functions. Early clinical experience has shown that simultaneous application of ultrasonic agitation increases the rate of laser cutting by a factor of two while excising the gingival tissue and that ultrasonic descaling of the root of the tooth is speeded up by a similar amount by simultaneous application of laser cauterization.

In one preferred embodiment, all three modes of operation are controlled by a single foot-operated activation switch which will operate the laser source, the ultrasonic source or both, depending on which mode the device is operating in according to a mode switch on the control console. In an alternative embodiment, the mode switch can be combined with the activation switch to create a multi-mode foot switch. In other alternative embodiments, the activation switch and/or the mode switch may placed on the handpiece for manual actuation. Other functions, such as air, irrigation and aspiration may also be combined with the handpiece for convenience and efficiency.

DETAILED DESCRIPTION OF THE INVENTION

Figure 1:
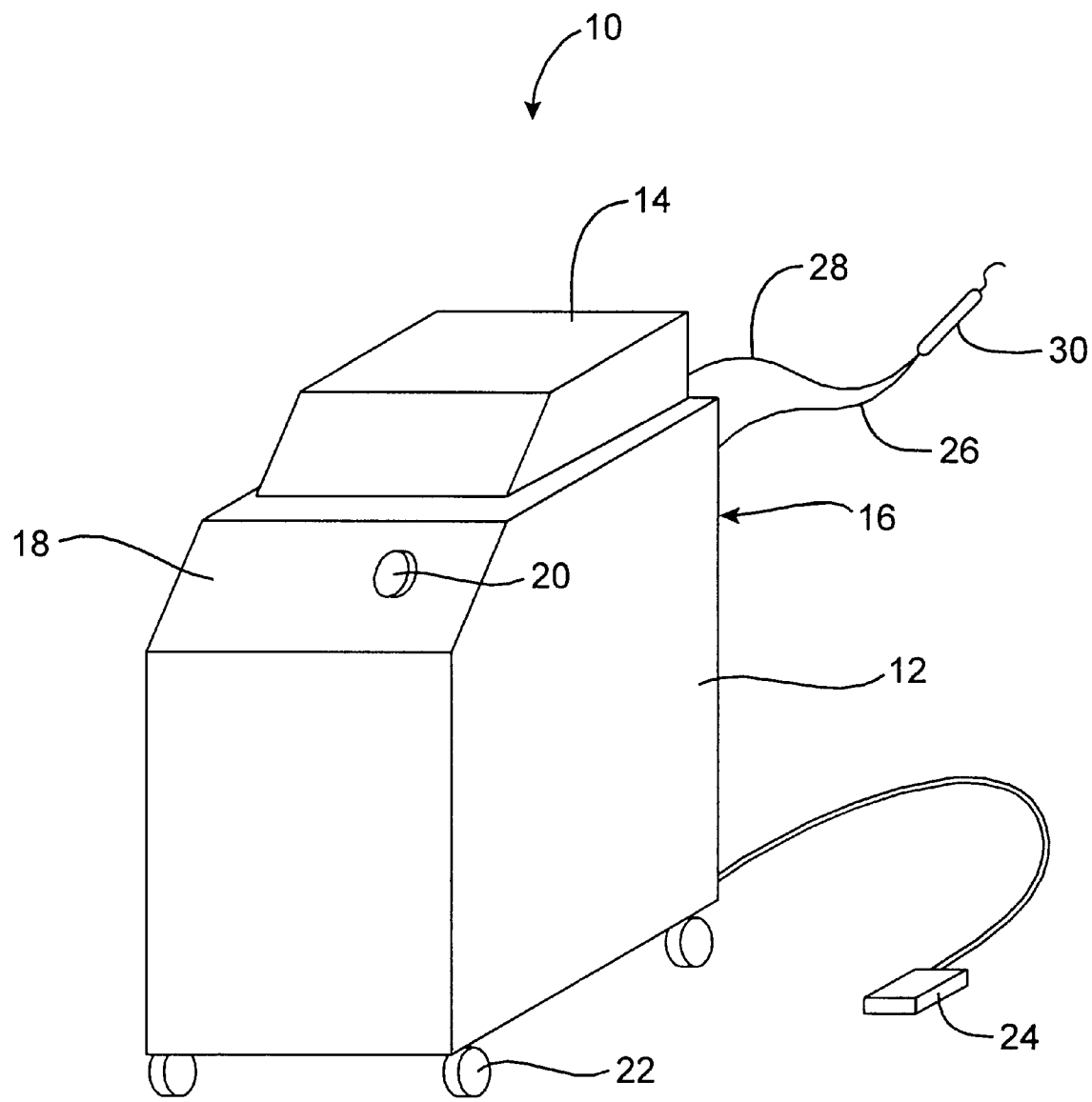
FIG. 1 shows the combined laser and ultrasonic device system, including the combination laser and ultrasonic source, the control console, the foot switch and the combined laser and ultrasonic delivery handpiece.

FIG. 1 shows the combined laser and ultrasonic device system 10 of the present invention. The system 10 includes a laser source 12 and an ultrasonic source 14 which have been combined together in a single unit 16. The laser source 12 may be any laser which is capable of excising and cauterizing tissue. The laser source 12 is preferably a laser which is deliverable via a flexible fiberoptic delivery system, for example a pulsed Nd:YAG laser, a holmium:YAG laser, an erbium laser, an excimer laser or other known laser source. Alternatively, a $CO_2$ laser may be used, but the flexible fiberoptic delivery system must be substituted with a reflective laser wave guide. Preferably, the laser source 12 is capable of delivering 1 to 100 watts of power at the distal end of the laser delivery device. In one particularly preferred embodiment, the laser source 12 is a variable pulse-width laser, such as described in U.S. Pat. No. 5,269,778, granted to John L. Rink and Howard S. Cohen, the specification of which is incorporated herein by reference in its entirety. The pulse width of this laser is variable from 100 microseconds up to 700 microseconds. It has been found that the tissue specificity made possible by this variable pulse-width laser has tremendous utility in dental applications that is not provided by prior art dental lasers that operate at only one fixed pulse width (typically 150 microseconds). More effective tissue ablation and coagulation can be achieved by choosing the optimum pulse width for the given application.

For example, coagulation of bleeders within the gums, which takes 1 minute with a pulse width of 150 microseconds, can be accomplished in approximately 3 seconds with a pulse width of 700 microseconds. The ultrasonic source 14 is preferably a self-tuning ultrasonic oscillator operating at 20 to 40 kilohertz. The ultrasonic power should be adjustable from 0 watts up to a maximum power of approximately 25 to 50 watts. Optionally, the frequency and bandwidth of the ultrasonic source 14 may also be adjustable. The combination laser and ultrasonic source 16 is preferably mounted on wheels or casters 22 for easy movement of the system.

The control console 18 of the system 10 has individual controls for the operating parameters of the laser source 12, such as pulsed or continuous wave mode, power, pulse width, pulse repetition rate, etc., and the operating parameters of the ultrasonic source 14, such as frequency, bandwidth and power. In addition, there is a mode switch 20 for switching the system 10 between three different modes of operation: 1) laser energy only, 2) ultrasonic energy only and 3) combined laser and ultrasonic energy. A foot-operated activation switch 24 operates the laser source 12, the ultrasonic source 14 or both, depending on which of the three operating modes the mode switch 20 is set on, when it is depressed by the operator's foot. In an alternative embodiment, the mode switch 20 can be combined with the activation switch 24 to create a multi-mode foot switch. In other alternative embodiments, the activation switch 24 and/or the mode switch 20 may placed on the handpiece 30 for manual actuation. Other functions, such as air, irrigation and aspiration may also be combined with the handpiece 30 and operated via a foot switch or a manual switch for convenience and efficiency. In one alternative embodiment of the system 10 envisioned by the inventors, the control console 18 will provide preprogrammed operating parameters for both the laser source 12 and the ultrasonic source 14 for various surgical applications, so that all of the parameters can be set with a single touch by the operator. Clinical experience with the system 10 in different surgical applications is expected to yield data about optimized parameters for each surgical application so that a library of preprogrammed settings can be created.

A combined laser and ultrasonic delivery handpiece 30 is connected to the laser source 12 by a flexible fiberoptic cable 26 and to the ultrasonic source 14 by an electrical signal cable 28. The flexible fiberoptic cable 26 uses a standard optical connector for connecting to the laser source 12. The electrical signal cable 28 may use a standard electrical connector or it may be hard wired to the ultrasonic source 14. In alternate embodiments, the flexible fiberoptic cable 26 and the electrical signal cable 28 may be combined together to create a single laser and ultrasonic umbilical cable with a combined connector.

Figure 2:
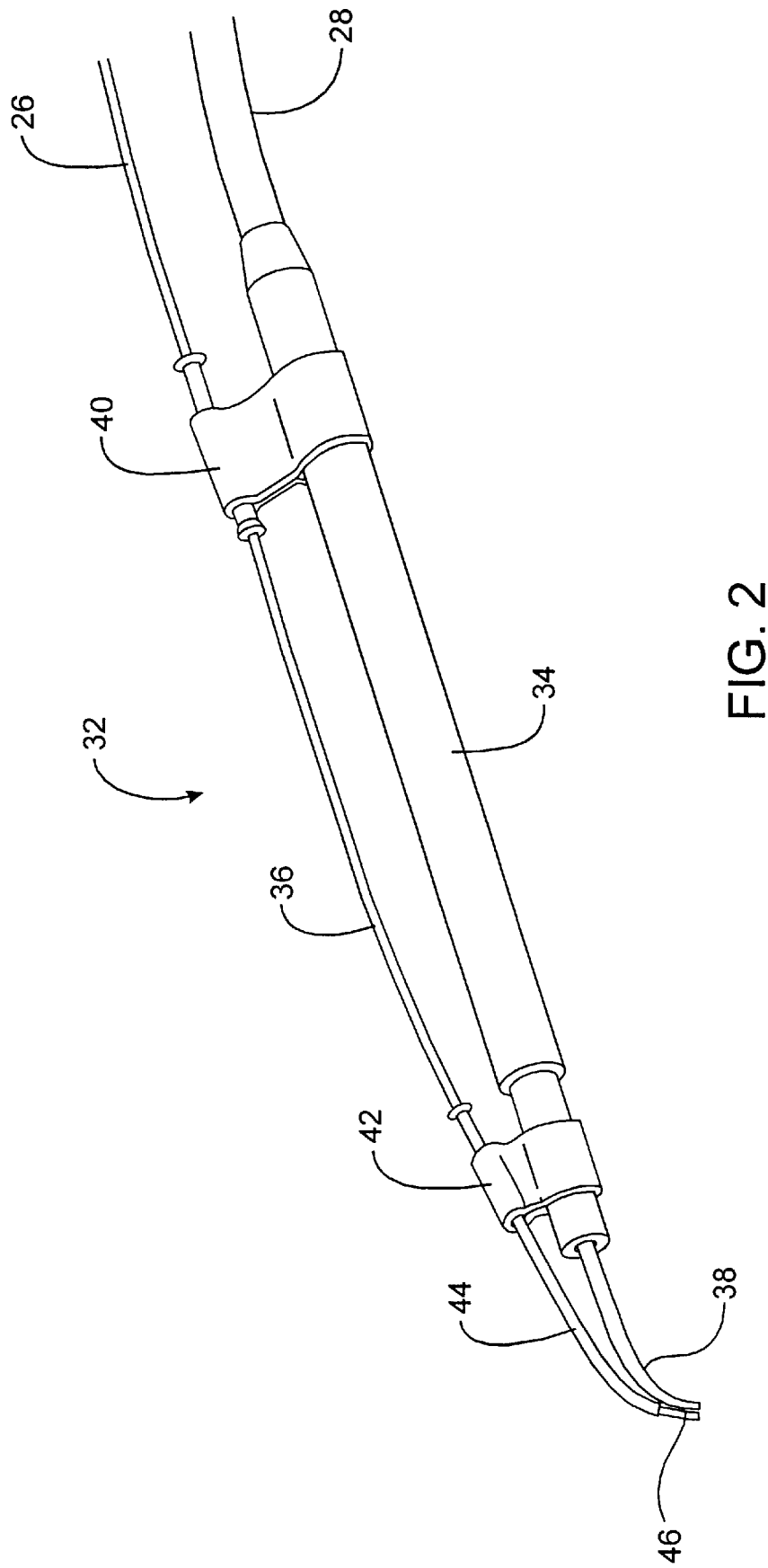
FIG. 2 shows a first embodiment of the combined laser and ultrasonic delivery handpiece.

FIG. 2 shows a first embodiment of the combined laser and ultrasonic delivery handpiece 32. In this embodiment, a known ultrasonic dental descaler handpiece 34 has been combined with a laser delivery optical fiber 36. The laser delivery optical fiber 36 may be continuous with the flexible fiberoptic cable 26 or the two may be removably connected by a high transmission efficiency optical coupling. The ultrasonic dental descaler handpiece 34 contains a magnetostrictive ultrasonic transducer which operates at 20 to 40 kilohertz. A dental descaling tip 38 is removably attached to the handpiece 34. The handpiece 34 and the dental descaling tip 38 may have an internal passageway which is attached to a pressurized water source for irrigation and for cooling of the magnetostrictive ultrasonic transducer. The laser delivery optical fiber 36 is a flexible optical fiber with a protective cladding and a fiber diameter from 100 to 1000 microns. A pair of mounting clamps 40, 42 attach the laser delivery optical fiber 36 to the handpiece 34. A malleable tubular extension 44 holds the distal end 46 of the optical fiber 36 in close proximity to and facing in the same direction as the distal end of the dental descaling tip 38. In this embodiment, the optical fiber 36 is positioned behind the dental descaling tip 38, which has been shown to be an effective arrangement for performing Laser E.N.A.P. based on early clinical experience. Alternatively, by adjusting the mounting clamps 40, 42, the optical fiber 36 may be positioned in front of or beside the dental descaling tip 38, if desired.

Figure 3:
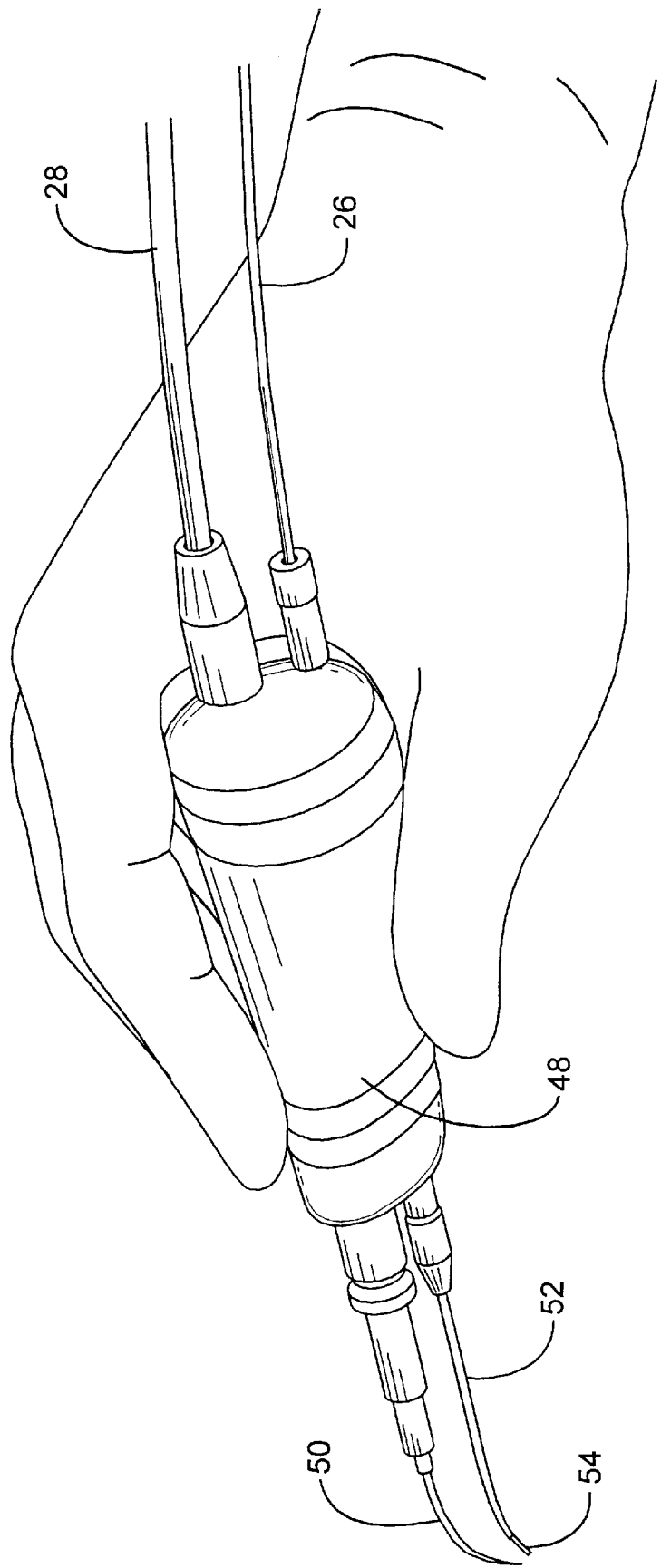
FIG. 3 shows a second embodiment of the combined laser and ultrasonic delivery handpiece.

FIG. 3 shows a second embodiment of the combined laser and ultrasonic delivery handpiece 48. In this embodiment, the ultrasonic transducer and the laser delivery optical fiber have been smoothly integrated into a unitary handpiece 48. The ultrasonic transducer in this case may be a magnetostrictive ultrasonic transducer or a piezoelectric ultrasonic transducer. A dental descaling tip 50 is removably attached to the handpiece 48 so that it efficiently receives ultrasonic energy from the ultrasonic transducer. A malleable tubular extension 52 holds the distal end of the optical fiber 54 in close proximity to and facing in the same direction as the distal end of the dental descaling tip 50. In this exemplary embodiment, the optical fiber 54 is positioned in front of the dental descaling tip 50, which may prove to be useful in certain clinical situations. Alternatively, the optical fiber 54 may be positioned behind the dental descaling tip 50, as in the embodiment of FIG. 2, or beside the dental descaling tip 50, if desired.

Figure 4:
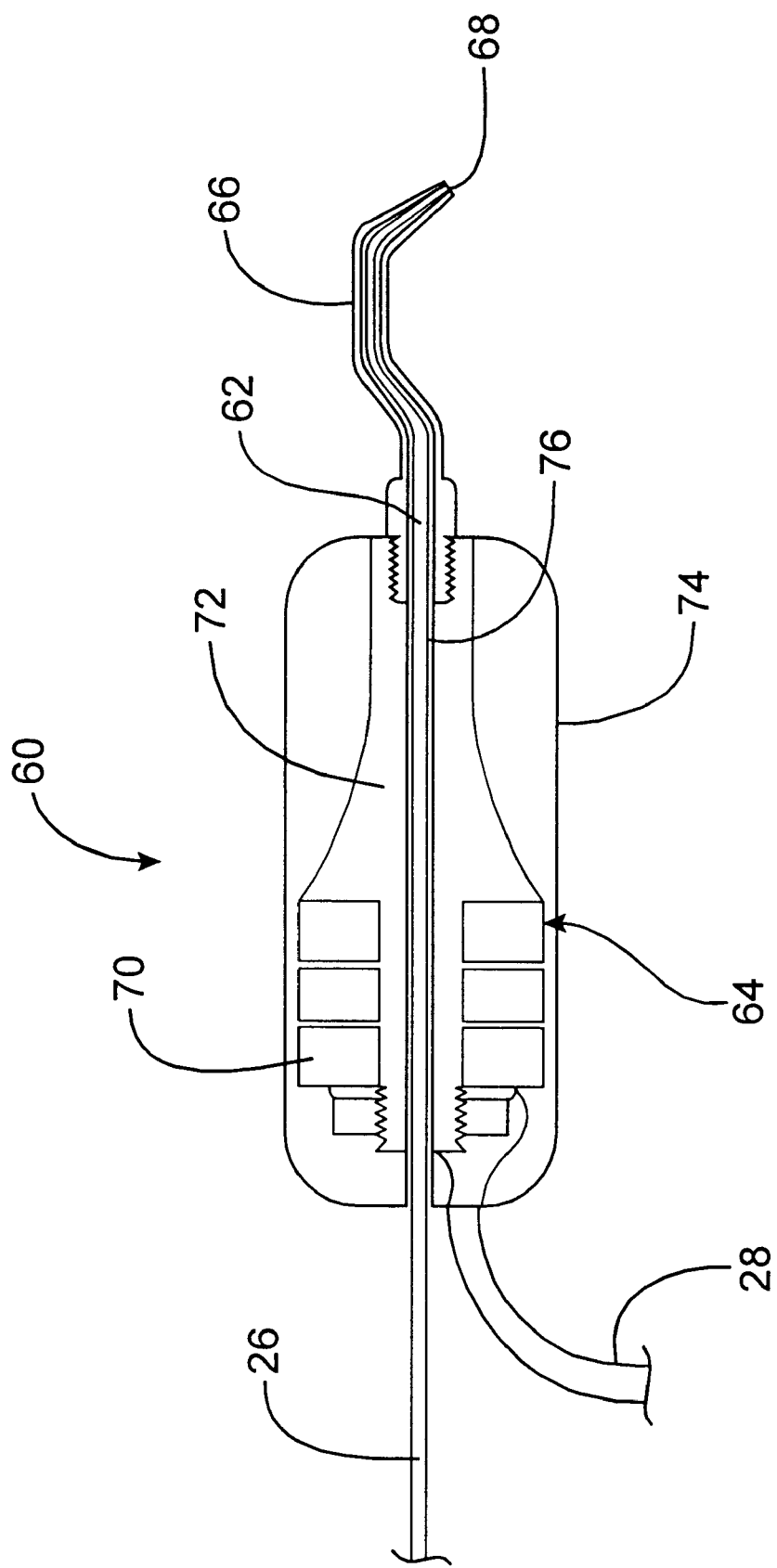
FIG. 4 shows a third embodiment of the combined laser and ultrasonic delivery handpiece.

FIG. 4 shows a third embodiment of the combined laser and ultrasonic delivery handpiece 60. In this embodiment, the laser delivery optical fiber 62 is positioned coaxially within an internal lumen 76 extending through a hollow ultrasonic transducer 64 and a hollow dental descaling tip 66. The distal end 68 of the laser delivery optical fiber 62 is positioned close to the distal end of the hollow dental descaling tip 66. The hollow ultrasonic transducer 64 may have one or more ring-shaped piezoelectric elements 70 wired in parallel and compressively mounted on a hollow ultrasonic concentrator horn 72 which increases the amplitude of the ultrasonic vibrations from the piezoelectric elements 70. Preferably, the dimensions of the ultrasonic transducer 64 are chosen to efficiently tune the transducer for vibrations in the range of 20 to 40 kilohertz. The ultrasonic transducer 64 and the laser delivery optical fiber 62 are enclosed within a handle 74.

The combined laser and ultrasonic device system of the present invention will find application in a wide variety of surgical applications. An improved method of performing the laser excisional new attachment procedure (Laser E.N.A.P.) is described below by way of example. For a description of standard Laser E.N.A.P., please refer to the enclosed U.S. Patent Application of Gregg and McCarthy for Laser Excisional New Attachment Procedure. This procedure can be performed faster and more efficiently by using the combined laser and ultrasonic device system of the present invention in place of the separate laser and ultrasonic devices described.

Figure 5:
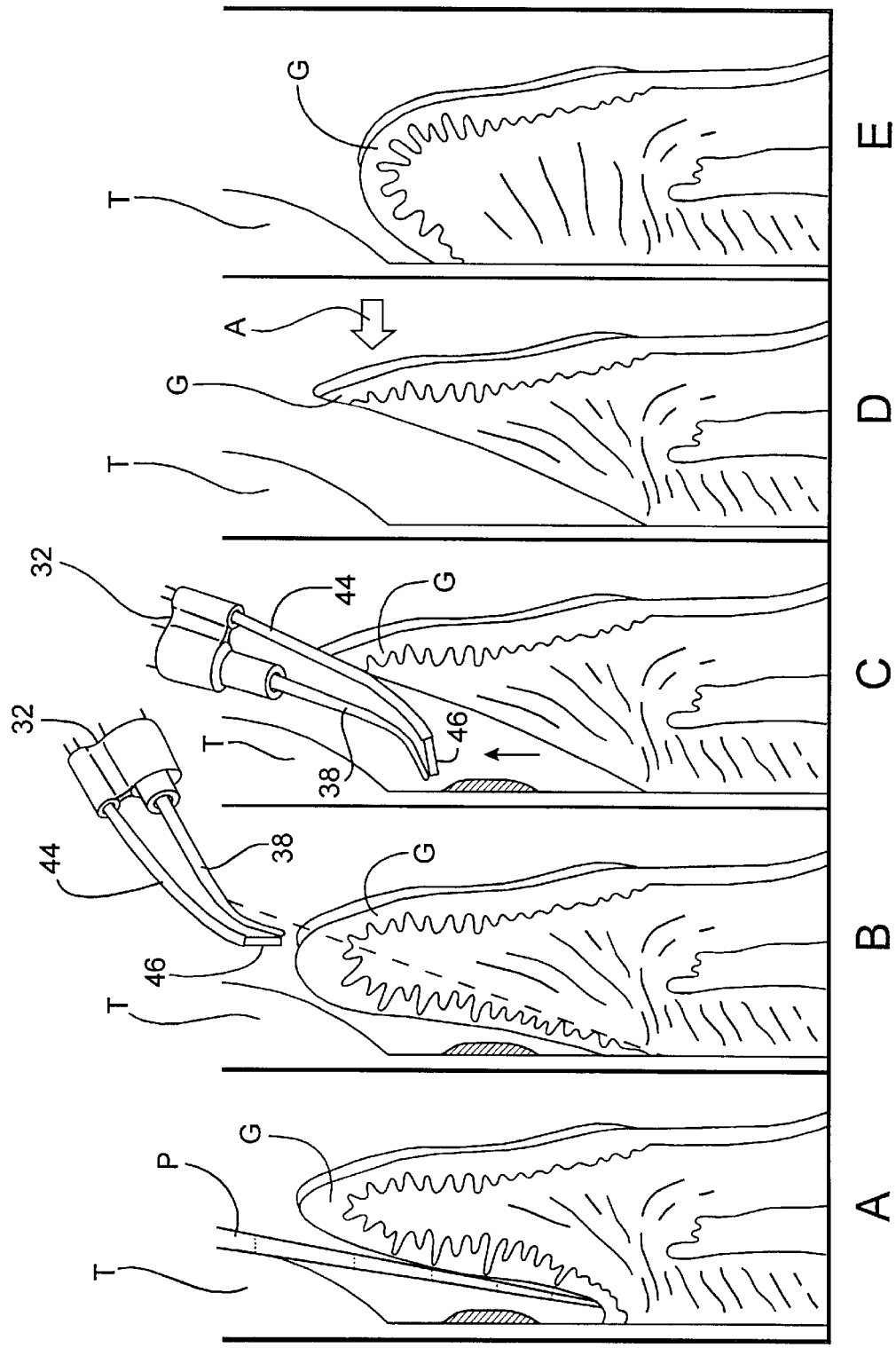
FIGS. 5A–E show the steps of the improved Laser E.N.A.P. method.

The improved method for performing Laser E.N.A.P. will be described with reference to FIGS. 5A–E. The first step of the method is to measure the depth of the gingival pocket with a standard probe P, as shown in FIG. 5A. Next, with the distal end of the optical fiber 44 of the handpiece 32 oriented along the long axis of the tooth T, the free gingival margin G is excised using laser energy to expose the root of the tooth T and to excise the inner pocket epithelium to the depth of the probe readings, as shown in FIG. 5B. The simultaneous application of ultrasonic energy using the dental descaling tip 38 doubles the speed of the laser cutting. Then, the root of the tooth T is ultrasonically descaled with the dental descaling tip 38, as shown in FIG. 5C. Simultaneous application of laser energy speeds up the ultrasonic descaling, as well as simultaneously cauterizing the tooth surface and the gingival pocket to prepare them for tissue welding and allowing the removal of large areas of granulation. Next, the gingival pocket is irrigated, preferably with a commercially available bactericidal solution such as Periodex® or PerioGard®, and the gingival tissue G is approximated to the root of the tooth T using compression for 2 to 3 minutes, as shown by the arrow A in FIG. 5D. The gingival tissue G is allowed to heal by secondary intention, thus reattaching the gingival tissue G to the tooth T and encouraging regeneration of the osteal attachment of the tooth, as shown in FIG. 5E.

While specific embodiments of the apparatus and the method of the present invention have been described in detail, the examples given are intended as illustrations of only a few of the many possible embodiments of the invention. Other variations and embodiments of the invention will no doubt occur to those of ordinary skill in the art upon reading and understanding the foregoing description. Thus, the scope of the invention should not be limited by the examples given, but should be determined by the appended claims and their legal equivalents.

What is claimed is:

1. Apparatus comprising:
   a source of laser radiation;
   a source of ultrasonic vibration;
   means for directing the laser radiation and the ultrasonic vibration onto a common target area; and
   a mode switch for selecting between three modes of operation: laser energy only, ultrasonic energy only and combined laser and ultrasonic energy for simultaneously directing laser energy and the ultrasonic energy onto the common target area.

2. The apparatus of claim 1 wherein the means for directing the laser radiation and the ultrasonic vibration onto a common target area comprises a combined laser and ultrasonic delivery handpiece having an ultrasonic vibrating tip mounted in close proximity to a laser delivery wave guide.

3. The apparatus of claim 2 wherein the laser delivery wave guide comprises an optical fiber.

4. The apparatus of claim 3 wherein the optical fiber is positioned within an internal lumen within the ultrasonic vibrating tip.

5. The apparatus of claim 1 wherein the means for directing the laser radiation and the ultrasonic vibration onto a common target area comprises a laser delivery wave guide and a malleable member for selectively positioning the laser delivery wave guide.

6. The apparatus of claim 1 wherein the source of laser radiation comprises a variable pulse width laser.

7. The apparatus of claim 1 wherein the source of laser radiation comprises a laser selected from the group consisting of holmium:YAG lasers, erbium lasers, excimer lasers, and $CO_2$ lasers.

8. The apparatus of claim 1 wherein the source of ultrasonic vibration comprises an ultrasonic transducer selected from the group consisting of magnetostrictive ultrasonic transducers and piezoelectric ultrasonic transducers.

9. The apparatus of claim 1 wherein the source of laser radiation comprises a Nd:YAG laser.

10. The apparatus of claim 1 further comprising an activation switch for selectively activating the source of laser radiation, the source of ultrasonic vibration or both the source of laser radiation and the source of ultrasonic vibration, according to the mode selected by the mode switch.

11. A combined laser and ultrasonic delivery handpiece comprising an ultrasonic vibrating tip mounted in close proximity to a laser delivery wave guide and a malleable member for selectively positioning the laser delivery wave guide.

12. The combined laser and ultrasonic delivery handpiece of claim 11 wherein the laser delivery wave guide comprises an optical fiber.

13. The combined laser and ultrasonic delivery handpiece of claim 12 wherein the malleable member comprises a malleable tube for selectively positioning the optical fiber.

14. The combined laser and ultrasonic delivery handpiece of claim 11 wherein the ultrasonic vibrating tip is coupled to an ultrasonic transducer selected from the group consisting of magnetostrictive ultrasonic transducers and piezoelectric ultrasonic transducers.

15. The combined laser and ultrasonic delivery handpiece of claim 11 further comprising a mode switch for selecting between three modes of operation: laser energy only, ultrasonic energy only and combined laser and ultrasonic energy.

16. A surgical method comprising:
   (a) generating laser radiation;
   (b) generating ultrasonic vibrations; and
   (c) simultaneously directing the laser radiation and the ultrasonic vibrations onto a common target area.

17. The method of claim 16 further comprising:
   (d) separately directing the laser radiation onto the common target area.

18. The method of claim 16 further comprising:
   (d) separately directing the ultrasonic vibrations onto the common target area.

19. The method of claim 16 wherein step (c) comprises directing the laser radiation and the ultrasonic vibrations through a combined laser and ultrasonic delivery handpiece onto the common target area.

20. The method of claim 16 further comprising:
   (d) sequentially directing the laser radiation and the ultrasonic vibrations onto the common target area.

21. The method of claim 16 wherein step (c) comprises directing the laser radiation and the ultrasonic vibrations onto a body tissue.

22. The method of claim 16 wherein step (c) comprises simultaneously directing the laser radiation and the ultrasonic vibrations onto a periodontal surface.

* * * * *